(12) United States Patent
Hazuda et al.

(10) Patent No.: US 12,005,072 B2
(45) Date of Patent: Jun. 11, 2024

(54) HIV DRUG COMBINATION FOR INCREASING BARRIER AGAINST RESISTANCE

(71) Applicant: Merck Sharp & Dohme LLC, Rahway, NJ (US)

(72) Inventors: Daria Jean Hazuda, Doylestown, PA (US); Ming-Tain Lai, Lansdale, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 606 days.

(21) Appl. No.: 17/258,649

(22) PCT Filed: Jul. 12, 2019

(86) PCT No.: PCT/US2019/041508
§ 371 (c)(1),
(2) Date: Jan. 7, 2021

(87) PCT Pub. No.: WO2020/018352
PCT Pub. Date: Jan. 23, 2020

(65) Prior Publication Data
US 2021/0283161 A1 Sep. 16, 2021

Related U.S. Application Data

(60) Provisional application No. 62/699,047, filed on Jul. 17, 2018.

(51) Int. Cl.
| | | |
|---|---|---|
| A61K 31/7076 | (2006.01) | |
| A61K 31/4439 | (2006.01) | |
| A61P 31/18 | (2006.01) | |

(52) U.S. Cl.
CPC ...... *A61K 31/7076* (2013.01); *A61K 31/4439* (2013.01); *A61P 31/18* (2018.01)

(58) Field of Classification Search
CPC .. A61K 31/7076; A61K 31/4439; A61P 31/18
See application file for complete search history.

(56) References Cited

U.S. PATENT DOCUMENTS

| 2013/0274276 A1 | 10/2013 | Haddad et al. |
| 2018/0055867 A1 | 3/2018 | Hazuda et al. |

FOREIGN PATENT DOCUMENTS

| WO | 2011120133 A1 | 10/2011 |
| WO | 2017139519 A1 | 8/2017 |
| WO | 2018005914 A1 | 1/2018 |

OTHER PUBLICATIONS

Lai et al., Antimicrobial Agents and Chemotherapy, 2022, 66, article e02223-21, 10 pages. (Year: 2022).*
Castro, H.C. et al., HIV-1 Reverse Transcriptase: A Therapeutical Target in the Spotlight, Current Medicinal Chemistry, 2006, 313-324, 13.
Delaugerre, C. et al., Resistance Profile and Cross-Resistance of HIV-1 Among Patients Failing a Non-Nucleoside Reverse Transcriptase Inhibitor-Containing Regimen, Journal of Medical Virology, 2001, 445-448, 65.
Feng, M. et al., In vitro resistance selection with doravirine (MK-1439), a novel nonnucleoside reverse transcriptase inhibitor with distinct mutation development pathways, Antimicrobial Agents and Chemotherapy, 2015, 590-598, 59(1).
Feng, Meizhen et al., Doravirine Suppresses Common Non-nucleoside Reverse Transcriptase Inhibitor-Associated Mutants at Clinically Relevant Concentrations, Antimicrobial Agents and Chemotherapy, 2016, 2241-2247, vol. 60, No. 4.
Gazzard, B., British HIV Association (BHIVA) guidelines for the treatment of HIV-infected adults with antiretroviral therapy, HIV Medicine, 2006, 487-503, 7.
Gotte, Matthias et al., HIV-1 Reverse Transcription: A Brief Overview Focused on Structure-Function Relationships among Molecules Involved in Initiation of the Reaction, Archives of Biochemistry and Biophysics, 1999, 199-210, vol. 365, No. 2.
Hammer, Scott M. et al., Treatment for Adult HIV Infection 2006 Recommendations of the International AIDS Society—USA Panel, JAMA, 2006, 827-843, 296.
Hazuda, D. et al., Understanding the resistance profile of the HIV-1 NNRTI Doravirine in combination with the Novel NRTTI MK-8591, 22nd International AIDS Conference, 2018, 1-9, N/A.
Hopkins, Andrew L. et al., Complexes of HIV-1 Reverse Transcriptase with Inhibitors of the HEPT Series Reveal Conformational Changes Relevant to the Design of Potent Non-Nucleoside Inhibitors, J. Med. Chem., 1996, 1589-1600, 39.
Michailidis, Eleftherios et al., Hypersusceptibility mechanism of Tenofovir-resistant HIV to EFdA, Retrovirology, 2013, 1-12, vol. 10, Art. No. 65.
Moore, John P. et al., New Targets for Inhibitors of HIV-1 Replication, Nature Reviews Molecular Cell Biology, 2000, 40-49, 1.
Oliveira, M. et al., M 184IN substitutions and E138K/M184IN double substitutions in HIV reverse transcriptase do not significantly affect the antiviral activity of EFdA, Journal of Antimicrobial Chemotherapy, 2017, 3008-3011, 72(11).
Rai, Mohammad A. et al., Emerging reverse transcriptase inhibitors for HIV-1 infection, Expert Opinion on Emerging Drugs, 2018, 149-157, 23:2.

(Continued)

*Primary Examiner* — Jonathan S Lau
(74) *Attorney, Agent, or Firm* — Eric Greenwald; John C. Todaro

(57) ABSTRACT

The instant invention relates to a method for reducing the risk for development of anti-viral treatment resistance due to an HIV mutation in a human subject infected with HIV, comprising administering EFdA in combination with one or more anti-viral agents.

15 Claims, 2 Drawing Sheets

(56) References Cited

OTHER PUBLICATIONS

Sato, A. et al., In vitro selection of mutations in Human Immunodeficiency virus type I reverse transcriptase that confer resistance to capravirine, a novel non nucleoside reverse transcriptase inhibitor, Antiviral Research, 2006, 66-74, 70(2).
Schneider, Michael F. et al., Patterns of the hazard of death after AIDS through the evolution of antiretroviral therapy: 1984-2004, AIDS, 2005, 2009-2018, 19.

* cited by examiner

HIV DRUG COMBINATION FOR INCREASING BARRIER AGAINST RESISTANCE

CROSS-REFERENCE TO RELATED APPLICATIONS

This application is a National Stage application of International Patent Application No. PCT/US2019/041508, filed Jul. 12, 2019, which claims priority to U.S. Provisional Patent Application No. 62/699,047, filed Jul. 17, 2018.

BACKGROUND OF THE INVENTION

Human immunodeficiency virus-type 1 (HIV-1) reverse transcriptase (RT) plays an essential role in the HIV-1 lifecycle by converting a single strand viral RNA into a double stranded pro-viral DNA via its polymerase and RNase H activities. (e.g., see, Gotte, M., et al., HIV-1 reverse transcription: A Brief Overview Focused on Structure-Function Relationships Among Molecules Involved in Initiation of the Reaction. *Archives of Biochemistry and Biophysics* 365:199-210, 1999). Therefore, inhibition of reverse transcriptase has been one of the primary therapeutic strategies for developing antiviral agents to suppress the replication of HIV-1 (e.g., see, Castro, H. C., et al., HIV-1 Reverse Transcriptase: A Therapeutical Target in the Spotlight. *Current Medicinal Chemistry* 13:313-324, 2006; Moore, J. P., and Stevenson, M., New Targets for Inhibitors of HIV-1 Replication. *Nature Reviews Molecular Cell Biology* 1:40-49, 2000.).

There are two classes of RT inhibitors: (1) nucleoside reverse transcriptase inhibitors (NRTIs) including nucleoside RTIs and nucleotide RTIs, which are active site inhibitors such as azidothymidine (AZT, zidovudine) and lamivudine (3TC), and (2) non-nucleoside reverse transcriptase inhibitors (NNRTIs) which are non-active site competitive inhibitors such as efavirenz (EFV), nevirapine (NVP), etravirine (ETR), and rilpivirine (RPV). The NNRTIs bind to a hydrophobic pocket in the p66 subunit of p66/p51 heterodimer of reverse trnsciptase (RT) at a distance of 10 Å from the polymerase active site (e.g., see, Hopkins, A. L., et al., Complexes of HIV-1 Reverse Transcriptase with Inhibitors of the HEPT Series Reveal Conformational Changes Relevant to the Design of Potent Non-nucleoside Inhibitors. *J Med. Chem.* 39:1589-1600, 1996). NNRTI binding causes conformational changes within p66 that reposition the active site residues into an inactive conformation, resulting in inhibition of the polymerization reaction.

The current standard of treatment for HIV-1 infected patients is highly active antiretroviral therapy (HAART), which is typically composed of 3 or more drugs with complementary mechanisms of actions. Patients undergoing HAART have experienced profound and continuous viral suppression, in many cases with substantial immune system recovery and halt of progression to clinical disease (e.g., see, Schneider, M. F., Gange, S. J., Williams, C. M., Anastos, K., Greenblatt, R. M., Kingsley, L., Detels, R., and Munoz, A. 2005. Patterns of the Hazard of Death After AIDS Through the Evolution of Antiretroviral Therapy: 1984-2004. *Aids* 19:2009-2018). Consensus guidelines for the use of HAART in antiretroviral-naïve subjects recommend the use of 2 NRTIs in combination with an integrase inhibitor, an NNRTI, or a boosted protease inhibitor)(e.g., see, Gazzard, B., et al., British HIV Association (BHIVA) Guidelines for the Treatment of HIV-infected Adults with Antiretroviral Therapy, *HIV Med.* 7:487-503. 2006; Hammer, S. M., et al., Treatment for Adult HIV Infection: 2006 Recommendations of the International AIDS Society-USA Panel. *JAMA* 296: 827-843, 2006).

The effectiveness of any antiretroviral agent, however, can be hampered by the emergence of resistance mutations in viruses. Moreover, a single mutation can lead to significant reductions in susceptibility to an HIV drug, often to all available inhibitors within the same class (e.g., see, Hammer, S. M. et al., Treatment for Adult HIV Infection: 2006 Recommendations of the International AIDS Society-USA Panel. *JAMA* 296:827-843, 2006; Delaugerre, C. et al., Resistance Profile and Cross-resistance of HIV-1 Among Patients Failing a Non-nucleoside Reverse Transcriptase Inhibitor-containing Regimen. *Journal of Medical Virology* 65:445-448, 2001).

Resistance mutations in viruses can be either genotypic or phenotypic. Specific mutations are associated with resistance to individual antiretroviral drugs (i.e. M184V is associated with 3TC). Viral strains with drug-specific mutations are said to have genotypic resistance to that drug. Phenotypic resistance is a measure of the actual impact of resistance on a drug's antiviral effect. If the virus is significantly less susceptible to a drug when actually exposed to it, it is said to have phenotypic resistance to that drug. Viral "susceptibility" or "sensitivity" is the degree to which the vims is suppressed by a drug, i.e., the extent to which that drug is still effective against the vims. Resistance is rarely an all-or-nothing phenomenon; different mutations (or combinations of mutations) confer varying degrees of drug resistance, ranging from minimal to very high. (From: www.aidsmap.com; HIV Treatments Directory/Drug Resistance/ Terminology.

As a result of resistance mutations in HIV-1 viruses, there is a significant unmet medical need for identifying new combinations of antiviral agents that can elevate the barrier for developing resistant viruses, thus providing more effective treatment for HIV-1 patients.

SUMMARY OF THE INVENTION

The instant invention relates to a method for reducing the risk for development of anti-viral treatment resistance due to an HIV mutation in a human subject infected with HIV, comprising administering EFdA in combination with one or more additional HIV antiviral drugs.

DETAILED DESCRIPTION OF THE INVENTION

The instant invention relates to a method for reducing the risk for development of anti-viral treatment resistance due to an HIV mutation in a human subject infected with HIV, comprising administering EFdA in combination with one or more additional HIV antiviral drugs.

In a class of the invention, the HIV mutation is selected from the group consisting of F227C, F227C with one or more NNRTI-associated mutations, F227C with one or more NRTI-associated mutations and combinations thereof.

In a class of the invention, the NNRTI-associated mutation is selected from the group consisting of A98G, L100I, K101E, K101P, K103N, K103S, V106A, V106I, V106M, V108I, E138A, E138G, E138K, E138Q, E138R, V179L, Y181C, Y181I, Y181V, Y188C, Y188H, Y188L, G190A, G190S, H221Y, L234I, P225H, F227C, F227L, F227V, M230L, M230I, P236L, Y318F and combinations thereof.

In a class of the invention, the NRTI-associated mutation is selected from the group consisting of M184V/I, K65R, M41L, D67N, K70R/E, T69inst, Q151M, L210W, T215Y/F, K219Q/E, L74V, Y115F and combinations thereof.

In a subclass of the invention, the HIV mutation is selected from the group consisting of F227C, A98G/F227C, V106I/F227C, V106M/F227C, C106M/F227C, V106/F227C/H221Y, A98G/V106I/H221Y/F227C or combinations thereof. As an example of the invention, the HIV mutation is F227C. As another example of the invention, the HIV mutation is A98G/F227C. As another example of the invention, the HIV mutation is V106I/F227C. As another example of the invention, the HIV mutation is C106M/F227C. As another example of the invention, the HIV mutation is V106/F227C/H221Y. As another example of the invention, the HIV mutation is A98G/V106I/H221Y/F227C.

As noted above, the present invention is directed to a method for reducing the risk for development of anti-viral treatment resistance due to an HIV mutation in a human subject infected with HIV, comprising administering EFdA in combination with one or more additional HIV antiviral drugs. An "HIV antiviral drug" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an HIV antiviral drug is effective in treating, preventing, or delaying the onset or progression of HIV infection or AIDS and/or diseases or conditions arising therefrom or associated therewith. For example, EFdA may be effectively administered, whether at periods of pre-exposure and/or post-exposure, in combination with effective amounts of one or more HIV antiviral drugs useful for treating HIV infection or AIDS. Suitable HIV antiviral drugs for use in combination with EFdA include, for example, those listed in Table A as follows:

TABLE A

| Name | Trade Name |
|---|---|
| abacavir, ABC | Ziagen ® |
| abacavir + lamivudine | Epzicom ® |
| abacavir + lamivudine + zidovudine | Trizivir ® |
| amprenavir | Agenerase ® |
| atazanavir | Reyataz ® |
| AZT, zidovudine, azidothymidine | Retrovir ® |
| darunavir | Prezista ® |
| ddC, zalcitabine, dideoxycytidine | Hivid ® |
| ddI, didanosine, dideoxyinosine | Videx ® |
| ddI (enteric coated) | Videx EC ® |
| delavirdine, DLV | Rescriptor ® |
| dolutegravir | Tivicay ® |
| doravirine | |
| efavirenz, EFV | Sustiva ®, Stocrin ® |
| efavirenz + emtricitabine + tenofovir DF | Atripla ® |
| emtricitabine, FTC | Emtriva ® |
| emtricitabine + tenofovir DF | Truvada ® |
| emvirine | Coactinon ® |
| enfuvirtide | Fuzeon ® |
| enteric coated didanosine | Videx EC ® |
| etravirine, TMC-125 | Intelence ® |
| fosamprenavir calcium | Lexiva ® |
| indinavir | Crixivan ® |
| lamivudine, 3TC | Epivir ® |
| lamivudine + zidovudine | Combivir ® |
| lopinavir | |
| lopinavir + ritonavir | Kaletra ® |
| maraviroc | Selzentry ® |
| nelfinavir | Viracept ® |
| nevirapine, NVP | Viramune ® |
| rilpivirine, TMC-278 | Edurant ® |
| ritonavir | Norvir ® |
| saquinavir | Invirase ®, Fortovase ® |
| stavudine, d4T, didehydrodeoxythymidine | Zerit ® |

TABLE A-continued

| Name | Trade Name |
|---|---|
| tenofovir DF (DF = disoproxil fumarate), TDF | Viread ® |
| tipranavir | Aptivus ® |

Some of the drugs listed in the table are used in a salt form; e.g., abacavir sulfate, indinavir sulfate, atazanavir sulfate, nelfinavir mesylate.

In a class of the invention, the additional antiviral drug is doravirine, or a pharmaceutically acceptable salt thereof. In a subclass of the invention, the antiviral drug is doravirine.

The instant invention also relates to a combination of EFdA and doravirine for use in a method of reducing the risk for development of anti-viral treatment resistance due to an F227C HIV mutation in a human subject infected with HIV.

In an embodiment of the invention, 100 mg of doravirine is administered to a human subject infected with HIV.

In another embodiment of the invention, between 0.25 mg and 2.25 mg of EFdA is administered to a human subject infected with HIV. In a class of the invention, 0.25 mg of EFdA is administered to a human subject infected with HIV. In another class of the invention, 0.75 mg of EFdA is administered to a human subject infected with HIV. In a class of the invention, 2.25 mg of EFdA is administered to a human subject infected with HIV.

In a class of the invention, the HIV mutation exhibits hypersusceptibility to EFdA. Illustrating the invention is a method for reducing the risk for development of anti-viral treatment resistance due to an F227C HIV mutation in a human subject infected with HIV, comprising administering EFdA in combination with doravirine.

As used herein, the term "hypersusceptible" refers to a mutant virus exhibiting a lower EC50 when compared with wild type (WT) virus in the presence of an antiviral agent; in this situation, the mutant is described as being hypersusceptible to the antiviral agent.

As used herein, the term "susceptible" refers to a virus that can be suppressed by an antiviral agent; in this situation, the virus is described as being susceptible to the antiviral agent.

As used herein, the term "HIV mutation" refers to changes in the DNA sequence of a virus, either from natural evolution or under the inhibitory pressure of antiviral agents.

As used herein, the term "resistance selection" refers to the situation when a WT virus will develop mutation(s) to confer resistance to the antiviral agent(s) when treated with escalating concentrations of the antiviral agent(s).

Doravirine (DOR, MK-1439) is a NNRTI having the following structural formula:

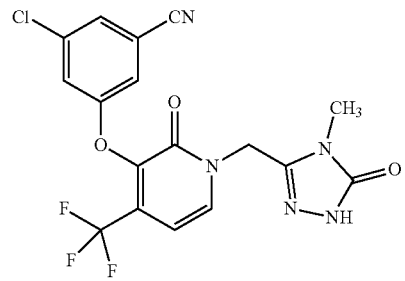

Doravirine

Doravirine showed excellent potency in suppressing the replication of wild type (WT) virus as well as K103N, Y181C, and K103N/Y181C mutant viruses in vitro with $EC_{50}$ of 12, 21, 31 and 33 nM, respectively, when measured in 100% normal human serum (NHS). Doravirine exhibited similar antiviral activities against 10 different HIV-1 subtype viruses (a total of 93 viruses). In addition, the susceptibility of a broader array of clinical-NNRTI-associated mutant viruses (a total of 96 viruses) to doravirine and other benchmark NNRTIs was investigated. The results showed that the mutant profile of doravirine was superior overall to that of efavirenz (EFV) and comparable to that of etravirine (ETR) and rilpivirine (RPV). See Lai, Ming-Tain, et al., In Vitro Characterization of MK-1439, a Novel HIV-1 Nonnucleoside Reverse Transcriptase Inhibitor. *Antimicrobial Agents and Chemotherapy* 58(3): 1652-1663, 2014.

Inhibitory quotients (IQs) were calculated by determining the ratio of the clinical trough concentration over the antiviral $EC_{50}$ of various viruses. IQs have been employed to predict the potential efficacy of anti-viral agents. Therefore, IQs were determined to assess the potential for DOR to suppress NNRTI-associated and RPV specific mutants at concentrations achieved at the clinic, DOR displayed IQ values of 39, 27 and 25 against K103N, Y181C, and K103N/Y181C respectively. In contrast, RPV exhibited IQ values of 4.6, 1.4, and 0.8, and EFV showed IQ values of 2.5, 60, and 1.9 against these viruses, respectively. DOR also displayed higher IQ values than RPV and EFV against other prevalent NNRTI-associated mutants with the exception of Y188L.

To understand potential mutation(s) that may evolve in the clinical settings, the resistance selection was conducted with escalating concentrations of DOR; the V106A mutant led two mutation pathways, followed by the emergence of F227L and L234I substitutions subsequently. See Feng, Meizhen, et al., In Vitro Resistance Selection with Doravirine (MK-1439), a Novel Nonnucleoside Reverse Transcriptase Inhibitor with Distinct Mutation Development Pathways. *Antimicrobial Agents and Chemotherapy* 59(1): 590-598-1663, 2015. In two Phase 3 clinical trials evaluating the safety and efficacy of DOR, it was observed that seven of 747 (0.9%) participants developed NNRTI resistance-associated mutations. For these seven patients, the majority of the viruses identified in the patients harbored F227C substitution.

Site-directed mutagenesis (SDMs) were generated for the substitutions V106I/F227C, V106I/H221Y/F227C, A98G/V106I/H221Y/F227C, and V106M/F227C and their susceptibility to NNRTIs was evaluated. Most of the mutants conferred a high level of resistance to DOR with a fold change (FC)>100 (FC: mutant$_{EC50}$ versus WT$_{EC50}$).

The F227C mutant has not been shown to be hypersusceptible to other antiviral agents except Zidovudine (AZT), which is a common nucleoside reverse transcriptase inhibitor. The susceptibility of F227C mutant to AZT was evaluated, and the result showed that the mutant was approximately 10-fold more susceptible to AZT. However, no further information was available on the cause of hypersusceptibility of F227C mutant to AZT. To understand this hypersusceptibility further, we compared the x-ray structure of AZT/RT and EFdA/RT based modeling.

X-ray structures illustrated that AZT-MP and EFdA-MP adopt distinct binding modes in the HIVRT P site.

The compound 4'-ethynyl-2-fluoro-2'-deoxyadenosine (EFdA, also known as MK-8591), is a nucleoside reverse transcriptase translocation inhibitor (NRTTI), which is a new class of RT inhibitor having the following structure:

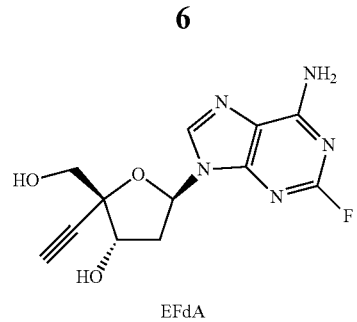

EFdA

As opposed to other currently marketed NRTIs, EFdA retains 3'-OH, which is more similar to the natural substrate than other NRTIs. As a result, studies have shown that EFdA-triphosphate (EFdA-TP) is a better substrate of HIV RT than the natural substrate dATP (e.g., see Michailidis, E., et al., Mechanism of Inhibition of HIV-1 Reverse Transcriptase by 4-Ethynyl-2-fluoro-2-deoxyadenosine Triphosphate, a Translocation-defective Reverse Transcriptase Inhibitor, J. Biol. Chem. 2009, 284 (51), 35681-35691), resulting in 10,000 times higher antiviral activity than EFddA (4'-ethynyl-2-fluoro-2'-dideoxyadenosine), the otherwise identical nucleoside lacking a 3'-OH. The 3'-OH of EFdA also contributes to its rapid and facile activation by the deoxycytidine kinase.

EFdA was tested in HIV-1 infected patients for a proof of concept study. The results showed that EFdA was capable of suppressing HIV replication for at least seven days when administered as a single dose as low as 0.5 mg. These results demonstrated that EFdA is highly potent in suppressing viral replication. When tested against most common doravirine-associated mutants containing F227C substitution, EFdA displayed better potency compared to WT virus. This unique feature suggests that combination of EFdA and doravirine should have a high barrier to the development of resistance and offer an effective treatment for HIV infected patients.

Taken together, these findings suggest the combination of doravirine with EFdA provides a unique antiviral treatment where the combination synergistically increases the barrier for the development of resistance.

Example 1

Susceptibility of SDM Derived Dor-Resistant Clinical Mutants to Nrtis

Figure 1:
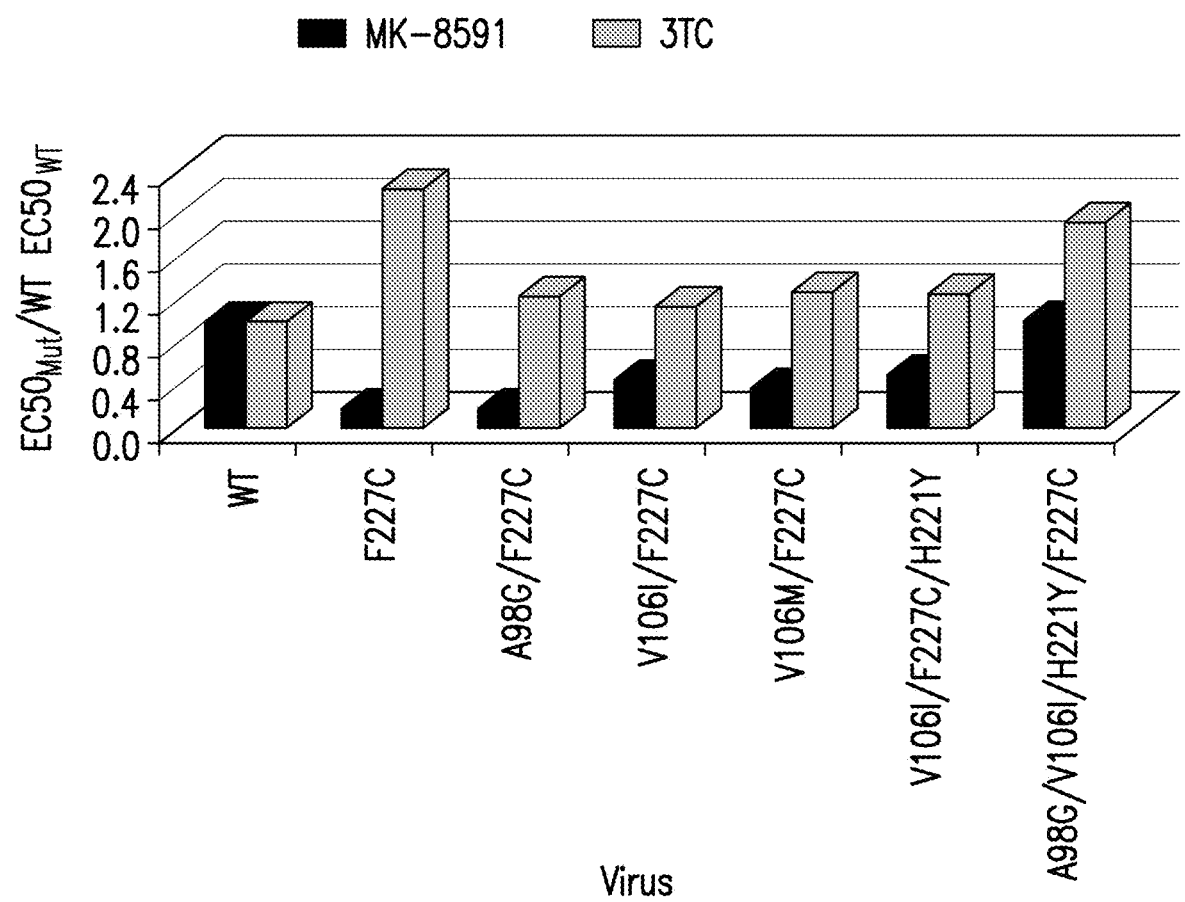
FIG. 1. Susceptibility of SDM derived DOR-resistant clinical mutants to NRTIs. As shown, the mutants exhibited similar susceptibility to 3TC compared with WT virus. In contrast, the mutants are hypersusceptible to EFdA with 2-5 fold increase in susceptibility except the quardruple mutant.

Common doravirine-associated mutants containing F227C substitution were derived from SDM. The experimental conditions for susceptibility evaluation are described in Lai, Ming-Tain, et al., In Vitro Characterization of MK-1439, a Novel HIV-1 Nonnucleoside Reverse Transcriptase Inhibitor. *Antimicrobial Agents and Chemotherapy* 58(3): 1652-1663, 2014. These mutants conferred more than 100-fold of resistance to DOR. The susceptibility of the mutants to EFdA and 3TC was also evaluated under the same conditions. As shown in the table below and in FIG. 1, the mutants exhibited similar susceptibility to 3TC compared with WT virus. In contrast, the mutants are hypersusceptible to EFdA with 2-5 fold increase in susceptibility with all mutants except the quardruple mutant.

| | Antiviral Potency (nM) | | Fold-change ($EC50_{mut}$/WT $EC50_{wt}$) | |
|---|---|---|---|---|
| | EFdA | 3TC | MK-8591 | 3TC |
| WT | 0.81 ± 0.029 (n = 5) | 601 ± 142 (n = 9) | 1.0 | 1.0 |
| F227C | 0.15 ± 0.026 (n = 11) | 1360 ± 94 (n = 4) | 0.18 | 2.26 |
| A98G/F227C | 0.15 ± 0.026 (n = 7) | 809 ± 146 (n = 4) | 0.18 | 1.25 |
| V106I/F227C | 0.35 ± 0.048 (n = 7) | 692 ± 212 (n = 4) | 0.44 | 1.15 |
| V106M/F227C | 0.30 ± 0.048 (n = 5) | 771 ± 62 (n = 4) | 0.37 | 1.28 |
| V106I/F227C/ H221Y | 0.40 ± 0.075 (n = 4) | 758 ± 244 (n = 4) | 0.49 | 1.26 |
| A98G/V106I/ H221Y/F227C | 0.81 ± 0.124 (n = 8) | 1160 ± 314 (n = 4) | 1.00 | 1.93 |

The results suggest that the common doravirine-associated F227C mutants will be suppressed by EFdA more effectively, thus the mutants are not expected to emerge with the combination of EFdA with doravirine. As a result, the regimen containing EFdA and doravirine should present a high barrier to the development of resistance.

Example 2

COMPARISON OF X-RAY STRUCTURE OF AZT/RT AND EFdA/RT The F227C mutant has not been shown to be hypersusceptible to other antiviral agents except Zidovudine (AZT). To understand this hypersusceptibility further, we compared the x-ray structure of AZT/RT and EFdA/RT based modeling.

Figure 2:
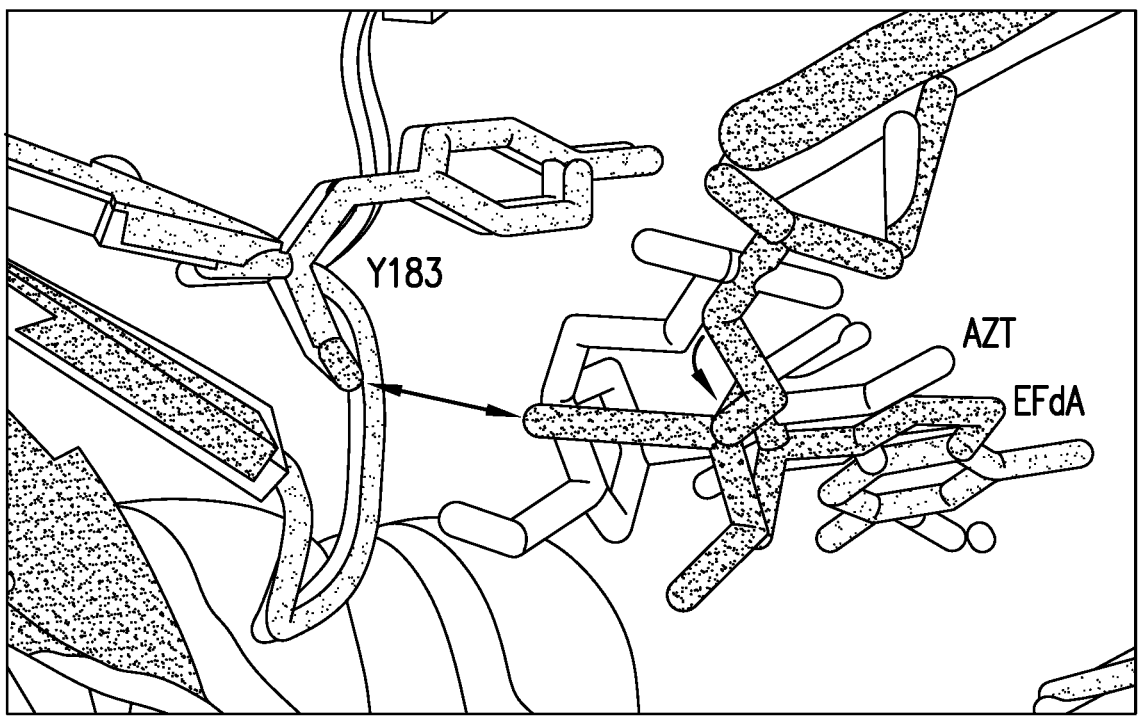
FIG. 2. X-ray structures of AZT/RT and EFdA/RT.

As shown in FIG. 2, X-ray structures illustrate that AZT-MP and EFdA-MP adopt distinct binding modes in the HIVRT P site. For AZT-MP/RT, see, Das, K, et al., HIV-1 reverse transcriptase complex with DNA and nevirapine reveals non-nucleoside inhibition mechanism. Nat Struct Mol Biol. 2012 Jan. 22; 19(2):253-9; For EFdA-MP/RT: EFdA/RT:, see, Salie, Z. L., et al., Structural basis of HIV inhibition by translocation-defective RT inhibitor 4'-ethynyl-2-fluoro-2'-deoxyadenosine (EFdA).Proc Natl Acad Sci USA. 2016 Aug. 16; 113(33):9274-9).

Specifically, the EFdA-MP sugar was shifted 2.8 Å, relative to AZT-MP, due to contact between the 4'-ethynyl group and protein surface. This resulted in a significant distortion of the primer strand DNA backbone. As can be shown, EFdA-MP and AZT-MP have distinct P site binding modes. Due to these significant differences in binding conformation, F227C hypersusceptibility to EFdA is not readily predictable from the structural comparison with AZT/RT.

Example 3

Combination of Efda and Doravirine Provide High Barrier to the Development of Resistant Mutation(s)

To support the contention that combination of EFdA and doravirine provide a high barrier to the development of resistant mutation(s), in vitro resistance selection studies (experimental conditions are described in Feng, Meizhen, et al., In Vitro Resistance Selection with Doravirine (MK-1439), a Novel Nonnucleoside Reverse Transcriptase Inhibitor with Distinct Mutation Development Pathways. *Antimicrobial Agents and Chemotherapy* 59(1): 590-598-1663, 2015) were conducted with escalation of concentration of doravirine/3TC and EFdA/doravirine with concentrations ranged from 0.25×EC50 to 8.0 EC50 (no viral breakthrough was observed at concentration 0.25×) using MT4-GFP cells. During the resistance selection, when viruses overcome the drug pressure with resistance mutation and start replicating, the cells will emit green fluorescence. At each passage, the medium was exchanged with fresh medium every 3-4 days. The results indicated that viruses can evolve resistant mutations even under high drug pressure of doravirine/3TC (4× EC50) as shown in the table below. In contrast, no viral breakthrough was observed at concentration of 4×EC50. More importantly, mutant containing F227C substitution was detected in the selection study of DOR/3TC combination, but the mutation was not selected in the presence of FEFdA/3TC combination. These results indicated that combination of FEFdA and doravirine confer higher level of barrier to the development of resistance mutation.

| Concentration (xEC50) | Selected Mutations | | | |
|---|---|---|---|---|
| | DOR/EFdA | DOR/3TC | DTG/3TC | BIC/3TC |
| 0.5x | V108I, M184I | V108I | WT | WT |
| 1x | V106A, V108I, M184I, P236L,Y318F | V106A, V108I, M184I, H221Y, L234I, Y318F | M184I | M184V |
| 2x | V106A, V108I, V184I | V90I, V106A, V108I, M184I, M230I, L234I, Y318F | M184I, M184V | M184I, M184V |
| 4x | Suppressed No breakthrough | D67N, V106A, M184I, F227C, F227V, M230I, L234I | M184I | M184I |
| 8x | Suppressed No breakthrough | Suppressed No breakthrough | M184I | Suppressed No breakthrough |

DOR—doravirine
3TC—lamivudine
BIC—bictegravir
DTG—dolutegravir

What is claimed is:
1. A method of reducing the risk for development of anti-viral treatment resistance due to an HIV mutation in a human subject infected with HIV, comprising administering an effective amount of EFdA in combination with one or more additional HIV antiviral drugs, wherein the additional antiviral drug is doravirine.

2. The method of claim 1, wherein the HIV mutation is selected from the group consisting of F227C, F227C with one or more NNRTI-associated mutations, F227C with one or more NRTI-associated mutations, and combinations thereof.

3. The method of claim 2 wherein the NNRTI-associated mutation is selected from the group consisting of L100I, K101E, K101P, K103N, K103S, V106A, V106I, V106M, V108I, E138A, E138G, E138K, E138Q, E138R, V179L, Y181C, Y181I, Y181V, Y188C, Y188H, Y188L, G190A, G190S, H221Y, L234I, P225H, F227C, F227L, F227V, M230L, M230I, P236L, Y318F, and combinations thereof.

4. The method of claim 2 wherein the NRTI-associated mutation is selected from the group consisting of M184V/I, K65R, M41L, D67N, K70R/E, T69inst, Q151M, L210W, T215Y/F, K219Q/E, L74V, Y115F, and combinations thereof.

5. The method of claim 2 wherein the HIV mutation is selected from the group consisting of F227C, A98G/F227C, V106I/F227C, C106M/F227C, V106/F227C/H221Y, and A98G/V106I/H221Y/F227C.

6. The method of claim 5 wherein the HIV mutation is F227C.

7. The method of claim 3 wherein the NRTI-associated mutation is selected from the group consisting of M184V/I, K65R, M41L, D67N, K70R/E, T69inst, Q151M, L210W, T215Y/F, K219Q/E, L74V, Y115F, and combinations thereof.

8. The method of claim 1 wherein the HIV mutation exhibits hypersusceptibility to EFdA.

9. The method of claim 1, wherein the doravirine is administered in an amount of 100 mg.

10. The method of claim 1, wherein the EFdA is administered in an amount of 0.25 mg.

11. The method of claim 1, wherein the EFdA and the doravirine are administered in a fixed combination of 0.25 mg EFdA and 100 mg doravirine.

12. A method of reducing the risk for development of anti-viral treatment resistance due to an F227C HIV mutation in a human subject infected with HIV, comprising administering an effective amount of EFdA in combination with doravirine.

13. The method of claim 12, wherein the doravirine is administered in an amount of 100 mg.

14. The method of claim 12, wherein the EFdA is administered in an amount of 0.25 mg.

15. The method of claim 12, wherein the EFdA and the doravirine are administered in a fixed combination of 0.25 mg EFdA and 100 mg doravirine.

* * * * *